(12) United States Patent
Bechtel et al.

(10) Patent No.: US 8,227,758 B2
(45) Date of Patent: Jul. 24, 2012

(54) DEVICE AND METHOD FOR DETERMINING THE CONVERSION POWER OF CONVERSION ELEMENTS

(75) Inventors: Helmut Bechtel, Roetgen (DE); Peter Schmidt, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 90 days.

(21) Appl. No.: 12/668,033

(22) PCT Filed: Jul. 14, 2008

(86) PCT No.: PCT/IB2008/052817
§ 371 (c)(1),
(2), (4) Date: Jun. 11, 2010

(87) PCT Pub. No.: WO2009/010915
PCT Pub. Date: Jan. 22, 2009

(65) Prior Publication Data
US 2011/0042584 A1     Feb. 24, 2011

(30) Foreign Application Priority Data
Jul. 16, 2007  (EP) ..................................... 07112499

(51) Int. Cl.
*G01J 1/58*  (2006.01)
(52) U.S. Cl. ................. 250/361 R; 250/362; 250/458.1; 250/459.1
(58) Field of Classification Search ............... 250/361 R, 250/458.1, 459.1, 336.1, 362
See application file for complete search history.

(56) References Cited

U.S. PATENT DOCUMENTS

| | | |
|---|---|---|
| 2002/0171911 A1 | 11/2002 | Maegawa |
| 2003/0075687 A1 | 4/2003 | Suzuki et al. |
| 2003/0203490 A1 | 10/2003 | Vuong |
| 2005/0121782 A1 | 6/2005 | Nakamura et al. |
| 2007/0045761 A1 | 3/2007 | Basin et al. |

FOREIGN PATENT DOCUMENTS

| | | |
|---|---|---|
| EP | 1605526 A2 | 12/2005 |
| WO | 2004068603 A2 | 8/2004 |

OTHER PUBLICATIONS

Moine et al: "VUV-Extended Measurements of Quantum Efficiency of Sodium Salicylate and of Some NBS Standard Phosphors"; Optical Materials, vol. 29, No. 9, pp. 1148-1152, 2007.

(Continued)

*Primary Examiner* — Mark R Gaworecki
(74) *Attorney, Agent, or Firm* — Mark L. Beloborodov (57) ABSTRACT

This invention relates to a device for determining the conversion power of conversion element, a method for performing these measurements and a method for producing pcLEDs with essentially the same color point applying said device and said method. The device comprises a light source (5), a sample holder (6) and a detector element (7), wherein the light source (5) illuminates the sample holder (6) with a primary light (41), the sample holder (6) is at least locally transparent for a primary light (41), suitable to mount the multitude of conversion elements (3) capable to partly convert the primary light (41) into a secondary light (42), and comprises suitable prevention means (62, 62*a*, 62*b*, 62*c*, 62*d*, 62*e*) to prevent a light guiding of the secondary light (42) from one mounted conversion element (3) through the sample holder (6) to another mounted conversion element (3), and the detector element (7) is suitable to measure the intensities of primary and secondary light (41, 42) for each conversion element (3) separately.

12 Claims, 9 Drawing Sheets

OTHER PUBLICATIONS

Husk T al: "Quantum Efficiency and Linearity of 16 Phosphors in the Soft-X-Ray Regime"; Journal of the Optical Society of America B, vol. 9, No. 5, pp. 660-663, May 1992.

Murakami et al: "Compound Semiconductor Lighting Based on InGaN Ultraviolet LED and ZnS Phosphor System"; 2000 IEEE International Symposium on Compound Semiconductors, pp. 449-454.

Yum T al: $Y_3Al_5O_{12}:Ce0.05$ Phosphor Coatings on a Flexible Substrate for Use in White Light-Emitting Diodes; Colloids and Surfaces A: Physicochem. Eng. Aspects, vol. 251, pp. 203-207, 2004.

DEVICE AND METHOD FOR DETERMINING THE CONVERSION POWER OF CONVERSION ELEMENTS

FIELD OF THE INVENTION

This invention relates to a device for color conversion measurements and to methods for performing these measurements and for producing phosphor converted LEDs (pcLEDs) with marginal variation of the color point between different pcLEDs.

BACKGROUND OF THE INVENTION

With the development of efficient light emitting diodes (LEDs) that emit blue or ultraviolet (UV) light, it has become feasible to produce LEDs that generate white light through phosphor conversion (pc) of a portion of the primary emission of the LEDs to longer wavelengths. These white light sources are so-called phosphor converted LEDs (pcLEDs). Conversion of primary emission of the LED to secondary emission with longer wavelengths is commonly referred to as down-conversion of the primary emission. "Primary light" or "primary emission" refers to light emitted by a light emitting diode (LED) and "secondary light" or "secondary emission" refers to light emitted by a phosphor, the so-called conversion element. In the following, the ratio between the non-converted (transmitted) primary light and the secondary light is denoted as light conversion power. The non-converted primary light combines with the secondary light to produce white light. The color point of the white light is determined by the light conversion power of the conversion element and the wavelength of the primary light. "Light conversion power" refers to the number of emitted photons of the light conversion element compared to the number of transmitted photons of a primary light. However, due to commonly present process variations the primary and secondary power ratios slightly deviate between individual pcLEDs resulting in visible deviations of color point. While the efficacy improved at lot in the last decade, the color consistency remains as one of the last obstacles for white LEDs to penetrate the general illumination market.

Before mounting the conversion elements current pcLED manufactures classify the LEDs (so-called binning) according to the characteristics of the emitted primary light, e.g. according to the peak wavelength (wavelength of maximum intensity). However, after mounting of conversion elements comprising the same conversion material on top of the LEDs taken from one class (BIN), the resulting pcLEDs show a large variation of their color points. This effect is caused by a varying conversion power between individual conversion elements. Beside the composition of a conversion material, the conversion power depends on additional parameters such as material density, scattering behavior and geometrical properties. Current process tolerances during production of conversion elements comprising the same conversion material lead to visible variations of the conversion power between individual conversion elements. Therefore also the conversion element needs to be classified before mounting it to a LED (so-called binning).

EP 1605526 discloses a pcLED, where the conversion element is produced in a sheet that is separated into individual conversion elements, which are bonded to LEDs to form pcLEDs. The conversion elements are selectively matched with a semiconductor LED to produce a desired mixture of primary and secondary light resulting in a desired color point of the pcLED. To determine the conversion properties of each conversion element, a sheet consisting of several conversion elements is illuminated with primary light and the mixture of converted and primary light is measured. Measurements performed on sheets of conversion elements are advantageous with respect to a short measuring time but the measurement accuracy is not sufficient.

Measurements performed on single conversion elements avoid this problem, but are time-consuming and therefore not preferred. The required time to measure a certain number of conversion elements increases significantly and prevents an application in mass production. Additionally, the construction of the sample holder may influence the measuring result by shading and/or reflecting effects resulting in an inaccurate primary to secondary light intensity ratio.

Matching of conversion elements with inaccurate determined conversion power to semiconductor LEDs leads to varying color points between different pcLEDs. To penetrate the general illumination market, a better color consistency of pcLEDs is required.

SUMMARY OF THE INVENTION

It is therefore an object of the present invention to provide a device and a method suitable to determine the conversion properties of a conversion element with an increased accuracy in order to produce pcLEDs with essentially the same color points.

This object is solved by a device for determining the light conversion power of a multitude of conversion elements comprising a light source, a sample holder and a detector element, wherein
- the light source is suitable to illuminate the sample holder with a primary light,
- the sample holder is at least locally transparent for the primary light, suitable to mount the multitude of conversion elements capable to partly convert the primary light into a secondary light, and comprises suitable prevention means to prevent a light guiding of the secondary light from one mounted conversion element through the sample holder to another mounted conversion element, and
- the detector element is suitable to measure the intensities of primary and secondary light for each conversion element separately, Here, the term "primary light" denotes the light, which will be partly converted by a conversion element mounted on the sample holder and is not limited to light emitted by LEDs. The light source can be any kind of light source emitting primary light similar to the primary light of the LEDs to be used to manufacture the corresponding pcLEDs. In any case the primary light of the said device light source must comprise at least a part of the wavelengths of the primary light of the LEDs capable for down-conversion by the conversion element. A preferred light source emits primary light with a peak wavelength within the wavelength range of the primary light emitted by the corresponding pcLED. The required color of the primary light depends on the desired application of the pcLED, e.g. the absorption spectrum of the conversion element. The light source may be a single light source or an array of light sources emitting the same primary light. To enable a light down-conversion the wavelength of the primary light can be any wavelength shorter than the wavelength of the secondary light and at least partially absorbed by the down-conversion element, which is determined by the material composition of the converting element. To obtain white light pcLEDs, the primary light may be blue light.

In an embodiment a diffuser plate is arranged between sample holder and light source to illuminate the sample holder with diffuse light. This avoids any angle dependence of the measured intensities of primary and secondary light and therefore increases the measurement accuracy. The required accuracy to align the detector to the sample holder is decreased. In another embodiment, the diffuser plate comprises a material, which absorbs secondary light. This is achieved for instance with diffuser plate with blue color filter material. Such a plate absorbs secondary light, e.g. emitted by a first conversion element towards the light source. An absorbing diffuser plate prevents a back-reflection of this secondary light to the sample holder in a direction where it could add to the secondary light intensity of a second conversion element. The diffuser plate can be arranged at any position between light source and sample holder. The diffuser plate may also be arranged on the light source. Light sources emitting diffuse light such as large organic LEDs do not require a diffuser plate. However, also here a blue plate can prevent back-reflection of secondary light.

Suitable detector elements determining the light conversion power are any detector elements able to provide a signal proportional to the incoming light intensity. Here, the conversion power is the ratio between the intensity of the secondary light emitted from the conversion element and the intensity of the primary light after passing the conversion element. The lateral resolution of the detector element has to be better than the minimum diameter of the emitting surface of the smallest conversion element to be able to relate the results to each conversion element separately. In one embodiment, the detector element comprises at least a first filter transparent either for primary light or for secondary light. The intensity of the correspondingly not directly determined intensity of the secondary or primary light can be derived from the measured total intensity of primary and secondary light and the measured intensity of either primary or secondary light. The conversion power of each conversion element results from the ratio between both intensities of primary and secondary light. Alternatively the detector element may also comprise a second filter transparent to the other secondary or primary light in addition to the first filter element (transparent to primary or secondary light). In this case, the intensities of primary and secondary light can be determined directly by performing the measurement in two steps: the first measurement with the first filter arranged within the light path between the sample holder with mounted conversion elements and the light detector and the second measurement with the second filter instead of the first filter. In case of conversion elements comprising a number of n different light converting materials in order to emit secondary light of n colors, the required number of filters has to be at least n. Obviously, also n+1 filters can be used to determine the intensities of all primary and secondary lights directly. Here the conversion power of a conversion element comprising different phosphor materials can be related to each phosphor material separately. In another embodiment the detector element comprises a CCD camera with a sufficient lateral resolution to determine the intensities of primary and secondary light for each conversion element simultaneously. To further increase the measurement accuracy, the measured intensity should result from averaging the measurements of more than 10 camera pixels.

The term "transparent for the primary light" corresponds to a transmission of more than 20%, preferably more than 50%, more preferred more than 70% of the primary light through the sample holder. The material of the transparent parts of the sample holder may be glass or plastic or any other transparent material. The prevention (suppression) of light guiding of secondary light from one conversion element to another conversion element (second conversion element) by the prevention means of the sample holder improves the measurement accuracy of the light conversion power of each conversion element significantly. The secondary light is isotropically emitted within the conversion element. This results in back reflection of all light with an incident angle to the interface between emitting surface and environment (usually air) larger than the critical angle for total reflection. At the interface to the sample holder, the difference of the refractive indices is much smaller compared to the interface between conversion element and air. Therefore essentially a large fraction of secondary light not emitted by the emitting surface of the conversion element is coupled (transmitted) into the sample holder. The emission through the side surfaces (usually perpendicular to the emitting surface) can be neglected due to total reflection effects and the small side surface area compared to emitting area and area facing towards the sample holder. Without prevention means this light will be guided through the whole sample holder and may be out-coupled again into a second conversion element and emitted through its emitting surface. In this case, the intensity of the secondary light emitted by the second conversion element is measured too high, because the intensity now is the sum of the secondary light created within the second conversion element and the secondary light created in a first conversion element but light-guided to the second conversion element via the sample holder. Correspondingly, the determined conversion power of the second conversion element would be too high and therefore the assignment of this conversion element to a certain LED would result in a pcLED with a color point different to the wanted color point. The corresponding multitude of pcLEDs would show a bad color consistence. It is not necessary to prevent light guiding of primary light to improve the measurement accuracy, because the conversion power does not depend on the total amount of primary light coupled into a conversion element.

The sample holder can exhibit any geometrical shape with any thickness suitable to mount conversion elements and to transmit the primary light. However, essentially flat geometries such as foils or plates are preferred to simplify the mounting of the conversion elements. The preferred thickness of the sample holder ranges from 0.001 mm to 10 mm. The lateral size of the sample holder should be suitable to mount several conversion elements on one sample holder in order to accelerate the measurements, e.g. by performing of simultaneous measurements of the light intensities with a detector element with a sufficient lateral resolution. The upper size limit mainly depends on the available size of the detector element.

In another embodiment the sample holder further comprises adhesive areas in order to mount conversion elements on the sample holder. On one hand the adhesive areas prevent any movement of the conversion elements during handling of the sample holder. On the other hand, the adhesive areas enable a good optical coupling between the conversion element and the sample holder. The term "good optical coupling" denotes a negligible difference of the optical coupling of different light-conversion elements. Compared to that, the amount of secondary light emitted through the side surfaces of the conversion elements directing towards neighbored conversion elements is negligible, because the secondary light not emitted through the emitting surface of the conversion element is probably coupled into the sample holder and not emitted through the side surfaces after several back reflections within the conversion element. The prevention means prevent further light guiding of this secondary light to other conversion elements via the sample holder.

In one embodiment the prevention means are located at the parts of the sample holder not covered with conversion elements. In this case, the back reflected secondary light is coupled into the sample holder but cannot pass the sample holder to an area covered with other conversion element. As an example, the prevention means can be arranged as a closed grid of any shape, e.g. a rectangular grid, a hexagonal grid, a dotted grid or any other regular or irregular shape. The closed grid defines cells, in which the conversion elements have to be mounted. Sample holders with prevention means arranged in such a structure can be equipped with conversion elements of any size and shape smaller than the cell size. This allows the use of the same sample holder for a large variety of conversion elements with different shapes and sizes. The prevention means can be any means, which are non transparent for secondary light.

In another embodiment the prevention means are at least one or more elements of the group of material absorbing at least the secondary light, a reflective material or a light scattering material with suitable scattering properties at least for secondary light. Here the absorbing material could be material absorbing all visible light or a filter material only absorbing the secondary light. In case of scattering material, the preferred scattering parameter (number of scattering events per length unit) of the material should be between $10\ cm^{-1}$ and $5000\ cm^{-1}$. The scattering parameter should be adapted to the available size within the sample holder between the areas to be mounted with conversion element. The transmission of secondary light through the prevention means should be less than 20%, preferably less than 10%, more preferred lesser than 5%. Depending on the wavelengths of the applied primary and secondary light, materials with suitable absorption, reflective or scattering properties are known by skilled people. Reflective materials can be metals e.g. Aluminum, Silver, Gold, Platinum, Paladium and others. Scattering is achieved by adding particles with a refractive index n1 to a matrix material with reflective index n2, with $abs(n2-n1) > 0.01$. Absorptive layers or compounds can be generated from coloured metal-oxides, -nitrides, -tantalates, -molybdates, metal salts incorporated into glass and/or organic dyes, i.e. organic compounds containing chromophores, which induce absorbtion of visible light by delocalized electrons. Also the combination of scattering and absorption is included here. E.g. incorporation of Cobaltaluminate (blue compound) particles into a transparent matrix material of a refractive index of about 1.4-1.6 generates a purely absorbing layer if the particles are smaller than 20 nm. For larger particle the layer is partially absorbing and partially scattering for visible light.

In another embodiment the prevention means are grooves within the sample holder. The shape and depth of the grooves have to be adjusted in order to decrease the transmission of secondary light from one side of the groove to the other side of the groove below 20%, preferably lesser than 10%, more preferred lesser than 5%. The grooves can be prepared within the sample holder before mounting the conversion elements, or the conversion elements are mounted onto the sample holder as a sheet of conversion elements and the grooves are prepared during separating the individual conversion elements from each other, e.g. by dicing techniques as applied in the semiconductor industry. In both cases, the grooves within the sample holder may have V-shapes, curved shapes or rectangular shapes or any other shape suitable to obtain a transmission below the above given values.

In a further embodiment the prevention means are arranged at least in the areas of the sample holder, which are covered with the conversion elements. In this case, the prevention means have to be transparent to primary light. This arrangement enables a more accurate prevention of light guiding of secondary light within the sample holder. It would be possible to mount the conversion element in a first step on top of the prevention means and in a second step the prevention means on a sample holder body in order to form the sample holder comprising the prevention means. Here, the conversion elements can be freely placed on the sample holder. The prevention means have a size equal or larger than the size of the conversion element surface facing towards the sample holder. In one embodiment the prevention means is a filter not transparent to secondary light. Depending on the wavelengths of the applied primary and secondary light, materials with suitable absorption properties are known to skilled people. In another embodiment, the prevention means extend over the whole sample holder. A sample holder non-transparent for secondary light enables the use of light sources 5 emitting light, which also contains secondary light. As a second advantage, the conversion elements can be freely placed on the sample holder non-transparent to secondary light without restrictions to shape and size as long as the conversion elements fit onto the sample holder.

This invention further relates to a method for determining the light conversion power of conversion elements with a device comprising a light source, a sample holder and a detector element according to claim 1 comprising the steps mounting the multitude of conversion elements on the sample holder, illuminating the sample holder with the multitude of conversion elements, measuring the intensities of the primary light transmitted through each of the conversion elements and the secondary light emitted from each of the conversion elements, determining the conversion power of each conversion element resulting from the ratio between the measured intensities of primary and secondary light of each conversion element, and classifying the conversion elements according to their conversion power.

The conversion elements are any rigid bodies ready for mounting to LEDs, e.g. ceramic plates, cups, phosphor powder layers, luminescent glass sheets, organic luminescent plates, etc. The conversion elements can by mounted onto the sample holder at the suitable location, for example by gluing. The gluing can be performed by an adhesive surface of the sample holder or by applying silicon between conversion element and sample holder. The conversion element may also be placed into recesses or cavities within the sample holder. Alternatively, the conversion elements may be mounted as continuous layer or sheet onto the sample holder and separated afterwards into single conversion elements, e.g. by dicing methods as known from the semiconductor industry, before performing the measurements. People skilled in the art may also consider alternative kinds of mounting.

The determination of the conversion power can be executed by any appropriate calculation unit as part of the detector element. Alternatively, the determined intensities of primary and secondary light or of one of the primary or the secondary light together with the total intensity of primary and secondary light (total light) may be transmitted to a computer in order to calculate the corresponding conversion power from the received intensity data. The sequence of measuring the intensity of primary and secondary or primary and total light or secondary and total light is not important to achieve accurate conversion power data. The conversion elements are classified in so-called BIN-classes according to the determined conversion power.

In another embodiment the intensities of the primary light transmitted through each of the conversion elements and the secondary light emitted from each of the conversion elements are measured simultaneously in order to accelerate the measurement speed (number of measured conversion elements per unit of time).

In another embodiment the mounting of the multitude of conversion elements further comprises the steps
  mounting of a continues sheet of conversion elements on the sample holder
  separating the conversion elements and preparing grooves within the sample holder to obtain the prevention means by a dicing process.

Here, the mounting of a continuous sheet of conversion elements, which are separated later, is easier and faster compared to the handling of each individual conversion element. Separate conversion elements are prepared by a dicing process as known from the semiconductor industry. Here, the dicing process combines the separation with the preparation of the prevention means within the sample holder. In this case, the prevention means are grooves within the sample holder.

The invention further relates to a method for producing a multitude of pcLEDs with essentially the same color point comprising the steps
  classifying LEDs according to the peak wavelength of their primary light.
  allocating the LEDs with conversion elements classified according to the method of claim 11 suitable to obtain a certain color point, and
  mounting together the allocated conversion elements and LEDs in order to obtain a multitude of pcLEDs with essentially the same color point.

The term "peak wavelength" denotes the wavelength with highest intensity within the range of emitted wavelengths. Suitable combinations of conversion elements and LEDs can be selected in order to produce pcLEDs emitting light composed of primary and secondary light with essentially the same color point. Here the color point is determined by the ratio between primary and secondary light. Essential for allocating a suitable conversion element to the LEDs is the accurate determination of the conversion properties of the conversion elements. As an example, for pcLEDs emitting white light composed of blue primary light and yellow secondary light, a color point variation Δu'v' lesser than 0.01 around a color point target value was achieved. The color point target value can be adjusted by varying the thickness of the conversion elements along the average light emission direction, the selection of light converting material and its amount within the conversion element or the color of the primary light provided by the LED. An advantage of the present invention is the possibility to produce LEDs with a color point close to the black body radiation curve with good reproducibility. These LEDs are very suited for illumination purposes in contrast to e.g. cold white LEDs with color point far away from the black body radiation curve.

The invention further relates to a sample holder and the use of the sample holder for determining the light conversion power of a multitude of conversion elements, which is at least locally transparent for a primary light, suitable to mount the multitude of conversion elements capable to partly convert the primary light into a secondary light separate from each other and comprises suitable prevention means to prevent a light guiding of the secondary light from one mounted conversion element through the sample holder to another mounted conversion element.

These and other aspects of the invention will be apparent from and elucidated with reference to the embodiment(s) described hereinafter. There embodiments will be described by way of example with the help of the accompanying drawing in which:

DETAILED DESCRIPTION OF EMBODIMENTS

Figure 1:
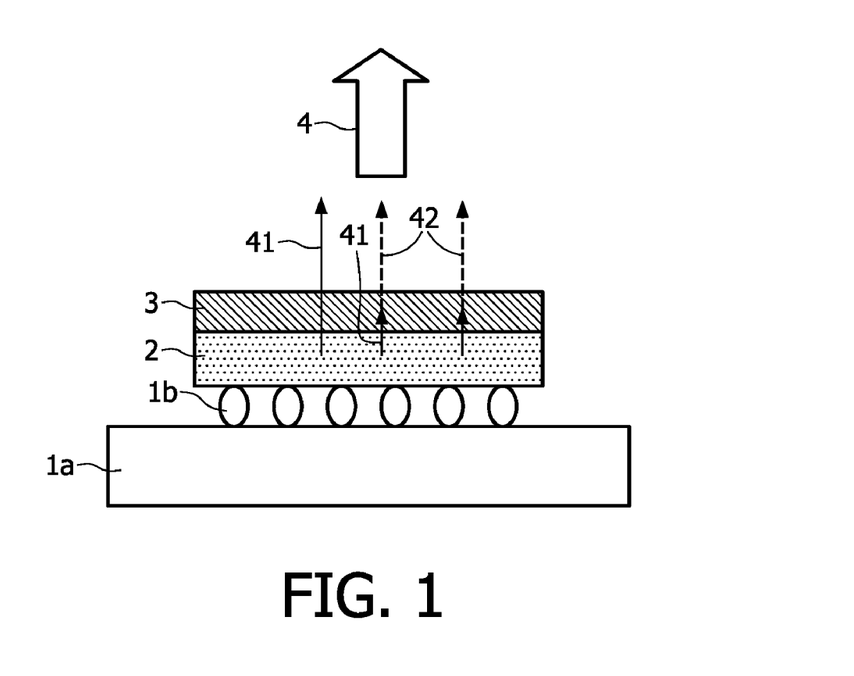
FIG. 1: schematic side view of a pcLED.

FIG. 1 shows a so-called phosphor converted LED (pc LED) with a LED 2 bonded to a substrate 1a via bonds 1b. The LED 2 emits primary light 41 within a certain wavelengths range with a maximum intensity at a certain wavelength within this range (peak wavelength). The peak wavelength corresponds to a certain color of the primary light 41. The conversion element 3 comprises converting material to absorb the primary light and to re-emit secondary light 42 with a wavelength longer than the primary light and is arranged on top of the LED 2. To achieve that all primary light emitted by the LED 2 passes the conversion element, the conversion elements may be shaped like caps also covering the side walls of the LED (not shown in FIG. 1). The secondary light has a maximum intensity at a certain wavelengths (peak wavelength) within a certain wavelength range. The peak wavelength corresponds to the color of the secondary light 42. As an example, blue primary light 41 and yellow secondary light 42 will result in white light 4 with a color point determined by the ratio between primary and secondary light 41 and 42.

Assuming identical emission properties of LEDs 2 and conversion elements 3 comprising identical converting material, the color point of the white light 4 is determined by the conversion power of the conversion element 3. It is not possible to manufacture conversion elements with exactly the same and desired conversion power. For instance, the thickness of the conversion element in emission direction (indicated by arrow 4 in FIG. 1) varies around an average value according to process tolerances. A thicker conversion element will convert more primary light to secondary light than a thinner conversion element. Also the light scattering properties varies between different conversion elements resulting in a deviating amount of emitted primary and secondary light compared to other conversion elements.

In order to keep the color point of pcLEDs constant in mass production, one can utilize the present variation of the peak wavelengths of the primary light between different LEDs to compensate for the variations of the conversion power of different conversion elements. The peak wavelength of the primary light of individual LEDs can deviate up to ±20 nm from the mean value of a large number of these LEDs. The peak wavelength of the primary light can easily be measured by people skilled in the art. The measured LEDs can by classified in so-called BIN classes (B) according to their peak wavelengths. Combing a LED of a certain BIN class with a conversion element of a suitable BIN class, the resulting pcLED emits light 4 very close to the desired color point. A multitude of these pcLEDs show a very low color point variations, e.g. color point variations Δu'v' lesser than 0.01 can be achieved.

Figure 2:
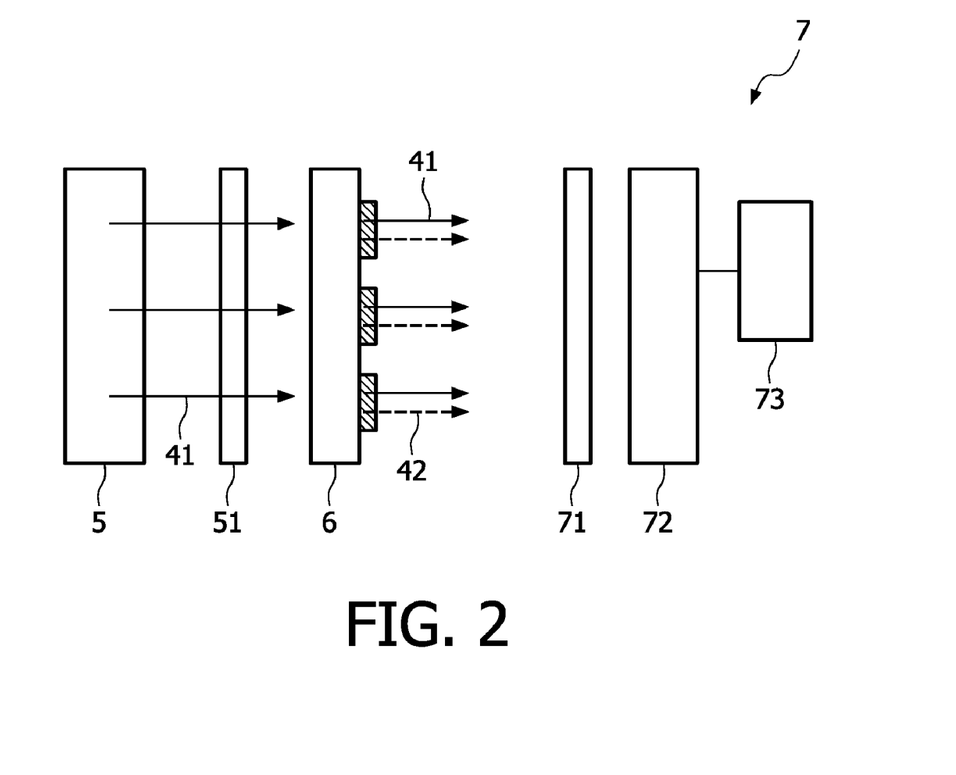
FIG. 2: schematic view of a device for determining the light conversion power according to the present invention.

FIG. 2 shows a schematic view of a device for determining the light conversion power according to the present invention. The light source 5 illuminates the sample holder 6 with primary light 41 corresponding to the primary light of a pcLED. The light source 5 may be any kind of light source or an array of light sources emitting at least primary light. In one embodiment, the light source 5 may be a LED or an array of LEDs used for pcLED production. In a preferred embodiment, the light source 5 emits diffuse blue primary light 41. The primary light incident to the sample holder 6 must not comprise secondary light 42. This can be achieved either with a light source 6 not emitting secondary light or with a light source 5 where an additional filter 51 non-transparent for secondary light is arranged between light source 5 and sample holder 6. In one embodiment, the sample holder itself can be the filter non-transparent for non-primary light, e.g. for secondary light. Such a filter 51 additionally prevents the back reflection of secondary light created within a first conversion element, out-coupled from the first conversion element into the sample holder and emitted from sample holder towards the light source. A back reflection of such secondary light from the filter 51 towards a second conversion element or towards a sample holder area, where this secondary light can be transmitted to a second conversion element should be prevented in order to achieve a good measurement accuracy for determining the conversion power of individual conversion elements. The absolute intensity of the primary light is not important for an accurate measurement of the conversion power. Intensity variations across the sample holder do not influence the ratio between primary and secondary light and are therefore acceptable.

As an example in FIG. 2, three conversion elements 3 are mounted on top of side of the sample holder 6 facing away for the light source 5 in order to determine its conversion power. In other embodiments, the conversion elements 3 could alternatively be mounted on the side of the sample holder 6 facing towards the light source 5. In the latter case the sample holder 6 must be also locally transparent for secondary light in order to transmit secondary light to the detector element. In both embodiments, the sample holder is locally transparent for primary light. For the transparent parts of the sample holder 6, glass, plastic or other suitable materials could be used. The number of mounted conversion elements 3 may be different for other sample holders 6.

The intensities of primary light 41 transmitted through the conversion elements and of secondary light 42 created within the conversion element 3 are measured by the detector element 7 comprising a sensor element 72 generating a signal proportional to the intensity of light. Both intensities can be measured directly in two steps. In a first step, a first color filter 71 only transparent for primary light 41 is placed between the conversion elements 3 and the sensor element 72. In this first step, the intensity of the primary light is measured. In a second step, the first color filter 71 is replaced by a second color filter 71 only transparent for secondary light 42 yielding the intensity of the secondary light 42. Alternatively to the use of a second filter, one can measure the total intensity of the emitted light (total light=primary light+secondary light) in a second step by removing the filter 71. The intensity of the secondary light 42 can be derived from the measured intensities of primary light 41 and total light 4. The same procedure applies to an alternative first measurement, where the first filter only transmits secondary light 42. Here, the intensity of the primary light 41 can be derived from the measured intensities of secondary light 42 and total light 4. Subsequently the ratio between the intensities of primary 41 and secondary light 42 can be calculated, e.g. by calculation means 73 either as part of the detector element 7 or by an external device, e.g. a computer. The calculation means 73 can also be used to derive the intensity of primary or secondary light in case measurements with only one filter 71. If the conversion elements 3 comprise n classes of converting materials re-emitting secondary light composed of n different colors, e.g. a first secondary light (e.g. green) and a second secondary light (e.g. red), n+1 measurements have to be performed applying at least n filter 71 only transmitting one corresponding color of secondary or primary light. Procedures suitable to remove, replace, or switch between the required color filters 71 are known by people skilled in the art.

Figure 3:
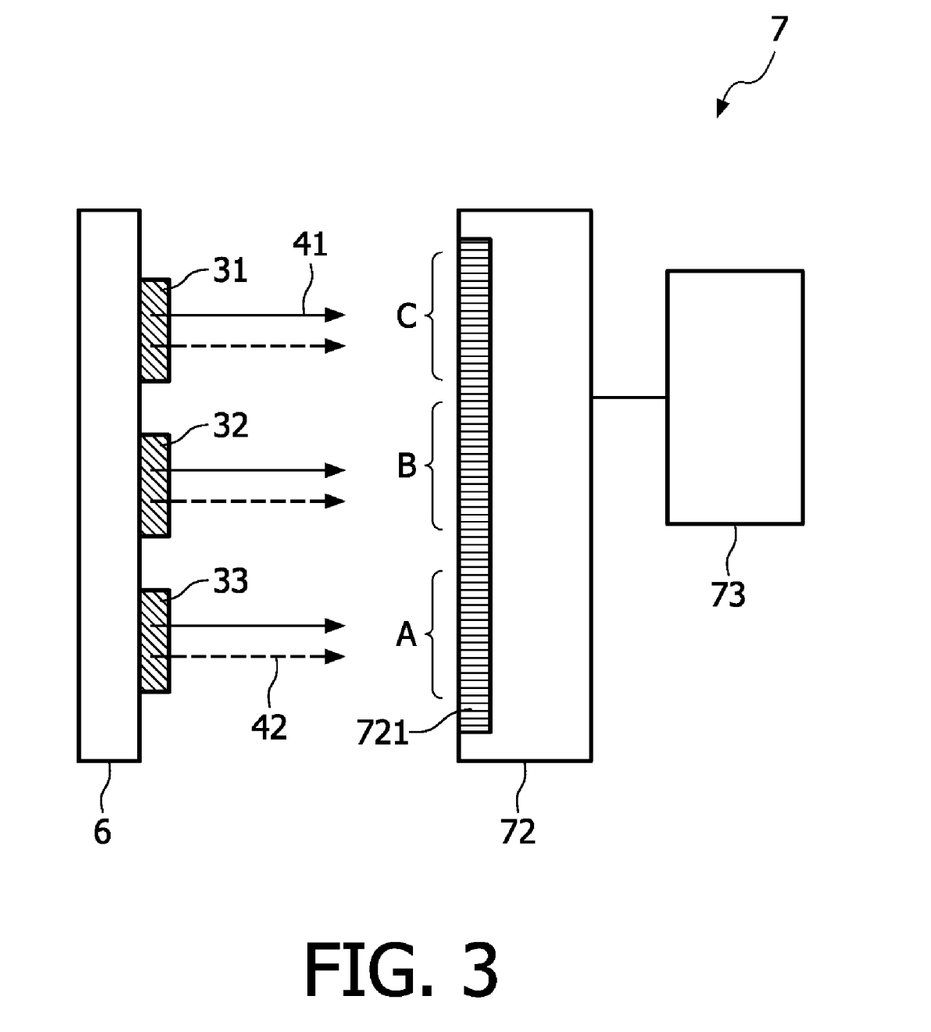
FIG. 3: schematic view of an embodiment of the detector element according to the present invention.

The primary and secondary light 41, 42 emitted by a conversion element 3 can be measured successively for each conversion element 3 by moving the detector element 7 or sensor element 72 across the sample holder 6. In a preferred embodiment, the measurements for each conversion element are executed simultaneously. Therefore the lateral resolution of the sensor element 72 has to sufficient to discriminate between primary and secondary light 41 and 42 emitted from different conversion elements 31, 32 and 33, as shown in FIG. 3. The distance between the sensor element 72 and the conversion elements 31, 32, 33 has to be either small enough that the light cones A, B and C of each conversion element do not overlap before reaching the sensor element 72 or the sensor element 72 has to comprises resolution means 721 to achieve a suitable lateral resolution even by overlapping light cones. Resolutions means 721 are known by people skilled in the art, e.g. grids shading of light with a to high incident angle to the surface of the sensor element 72 facing towards the sample holder 6. As an example, a CCD camera can be used as detector element 7. To achieve the required accuracy by determining the conversion power, it is preferred to use a CCD camera with more than 10 camera pixels to measure the light intensities.

Figure 4A:
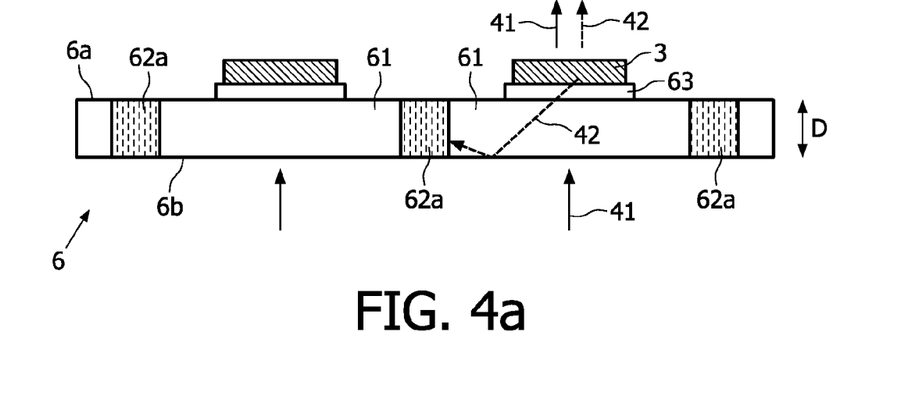
FIG. 4a: side view of an embodiment of the sample holder according to the present invention.
Figure 4B:
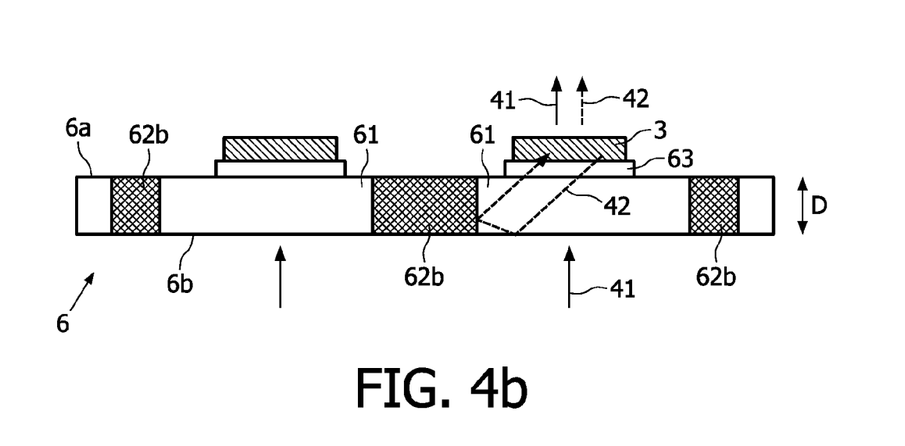
FIG. 4b: side view of another embodiment of the sample holder according to the present invention.
Figure 4C:
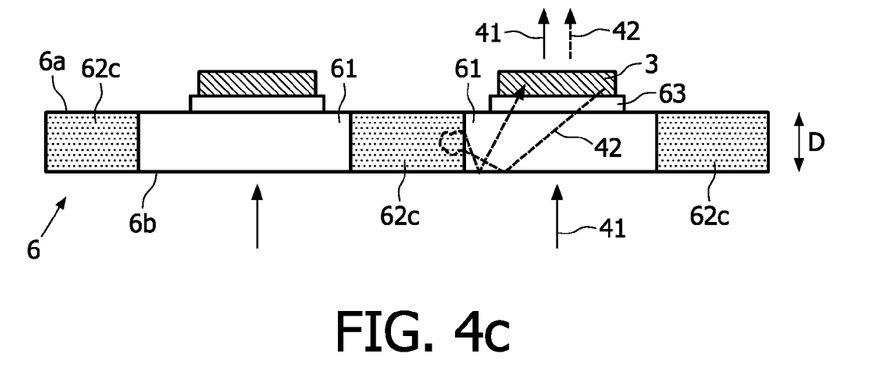
FIG. 4c: side view of another embodiment of the sample holder according to the present invention.
Figure 4D:
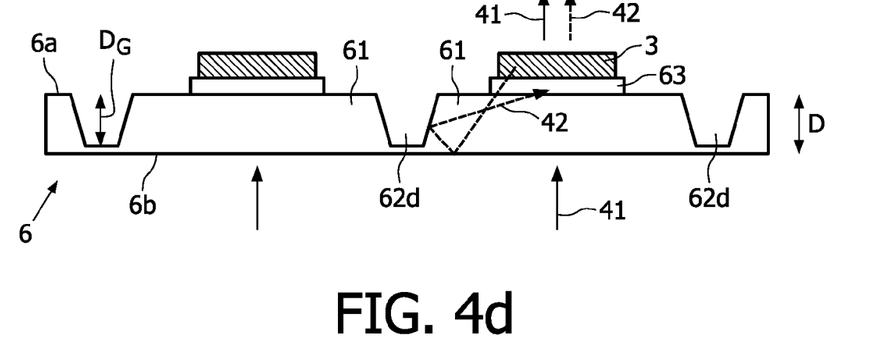
FIG. 4d: side view of another embodiment of the sample holder according to the present invention.

FIG. 4*a-d* show different embodiments of sample holders 6 comprising different kinds of prevention means 62*a*, 62*b*, 62*c*, 62*d*. The conversion elements 3 are mounted for instance via an adhesive layer or film 63 to the sample holder 6. The adhesive layer/film 63 must be transparent at least for primary light. The adhesive layer may be a layer of silicon or other suitable layer or films. Such an adhesive layer or film enables an easier handling of the sample holder, because the conversion elements are fixed to the sample holder. The prevention means 62a, 62b, 62c, 62d are arranged at areas of the sample holder not covered with conversion elements. The lateral size of the conversion elements 3 should to be equal or smaller than the distance between neighbored prevention means. The lateral size must not extend over the prevention mean around a conversion element 3. The area 61 of sample holder underneath the conversion element is an area transparent for primary light 41. The incident primary light 41 passes the sample holder 61 and the transparent adhesive layer and will be partly down-converted by the conversion element 3. A part of the secondary light will leave the conversion element through the surface facing towards the detector element (the emitting surface of pcLEDs). Another part of the secondary light will be coupled into the sample holder as indicated by an downwards directed arrow 42 in FIGS. 4a, 4b, 4c and 4d. Without prevention means, a major part of this light would be light guided through the hole sample holder and may leave the sample holder through another conversion element falsifying the to be measured conversion power of the latter conversion element. The prevention means 62a, 62b, 62c, 62d prevent or at least strongly suppress the transmission a secondary light 42 from one area 61 to a neighbored are 61. Therefore the prevention means preferably extend over the whole thickness D of the sample holder 6. In FIG. 4a, the prevention means 62a comprise light absorbing material at least capable to absorb secondary light 42. For instance suitable material may be a filter materials such as lighting filter from Lee Filters, or totally absorbing materials such as neutral density filter layers of carbon or thin metal layers, e.g. 5 nm Al. In FIG. 4b, the prevention means 62b comprise light reflecting material. For instance suitable materials may be any metallic material such as aluminium, titanium etc. In FIG. 4c, the prevention means 62c comprise light scattering material with a suitable scattering parameter. For instance such prevention means comprise small particles with a refractive index of more than 0.05 smaller or larger than the refractive index of the host material, e.g. the transparent material of the sample holder 6. A preferred scattering parameter (number of scattering events per length unit) of the material should be between 10 cm$^{-1}$ and 5000 cm$^{-1}$. In FIG. 4d, the prevention means 62d are grooves within the sample holder 6 extend from the side 6a of the sample holder 6 facing towards the detector element 7 into the sample holder. The shape and depth of the grooves has to be adjusted in order to decrease the transmission of secondary light from one side of the groove to the other side of the groove. The grooves can be prepared for example by dicing techniques as applied in the semiconductor industry. The shown shape of the grooves 62d is only one possible example, the grooves may also have V-shapes, curved shapes or rectangular shapes or any other shape suitable to obtain a transmission below the above given values. Furthermore, the grooves may be filled with light absorbing or light reflecting material. A major part of the secondary light incident to the surface of the sample holder 6a within the grooves will be reflected back due to an incident angle larger than the angle for total refection. The optical transition from an optical dense medium (sample holder) to air will redirect the out-coupled secondary light towards the detector element. However, the chance of the out-coupled light to enter a neighbored conversion element is very low. The transmission rate of secondary light from one conversion element to another secondary light depends on the remaining thickness $D_G$ of the sample holder 6 within a groove 62d. The minimum limit for the thickness $D_G$ is given by the stability of the sample holder material. The thickness of the prevention means in the direction perpendicular to the surfaces 6a, 6b of the sample holder 6 should be adjusted in order to decrease the transmission of secondary light 42 through the prevention means 62a, 62b, 62c, 62d to values below 5%. There is no strict upper limit for the thickness D of the sample holder 6 as long as it is transparent for primary light. The lower limit is set by the required stability of the sample holder. Preferred thicknesses of the sample holder are between 0.001 mm-10 mm.

Figure 5A:
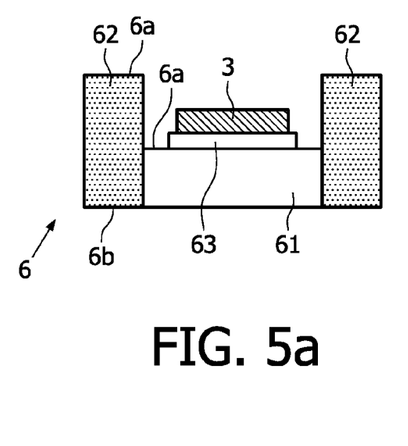
FIG. 5: side view of two other embodiment of the sample holder according to the present invention.
Figure 5B:
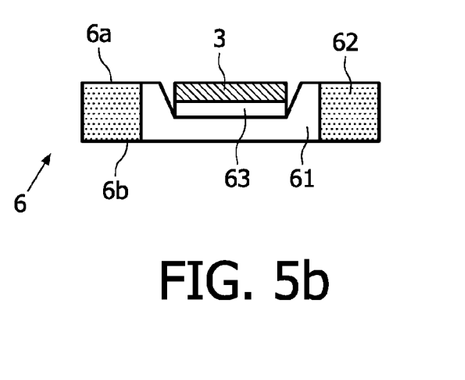

FIG. 5 shows two other embodiments of the sample holder 6, where the prevention means 62 can comprise at least one element of the group of absorbing, reflecting, scattering prevention means or grooves as prevention means. In FIG. 5a, the prevention means 62 extend over the emitting surface of the enclosed conversion element 3. This prevents the direct transmission of secondary light 42 from a side area face of one conversion element 3 towards the side face of a neighbored conversion element 3. The term "side face" denotes the surface of a conversion element 3 facing towards a neighbored conversion element 3 mounted on the sample holder 6. The conversion elements 3 may be mounted via onto the sample holder via an adhesive layer 63. FIG. 5b shows a conversion element 3 mounted within a recess in the sample holder 6. in other embodiments the recess may fit exactly to the shape of the conversion elements 3 in order to fix the conversion elements 3 onto the sample holder 6 without adhesive layers 63. In both cases, the area 61 of the sample holder below the conversion element is transparent at least to primary light 41.

Figure 6:
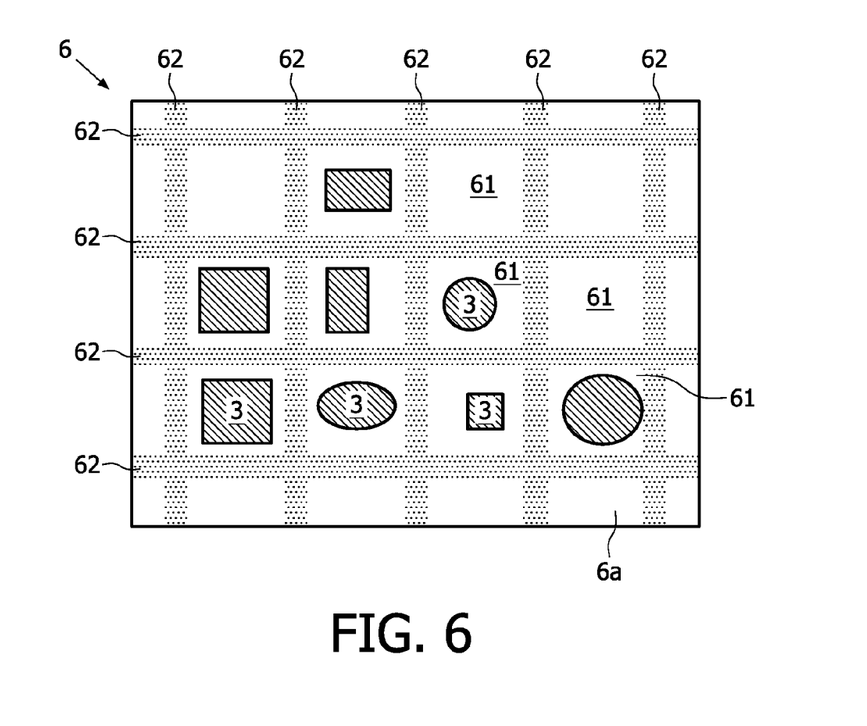
FIG. 6: top view of an embodiment of the sample holder according to the present invention.

FIG. 6 shows an example of a sample holder in top view. The propagation direction of the primary light 41 is perpendicular to the shown sample holder area 6. The prevention means 62 form closed areas 61 on the surface 6a where the sample holder is at least transparent for primary light 41. The conversion elements 3 are mounted within these cells. The conversion elements may have any shape and size as long as the conversion elements fit into such a cell. In other embodiments the cells may have other regular or irregular shapes.

Figure 7A:
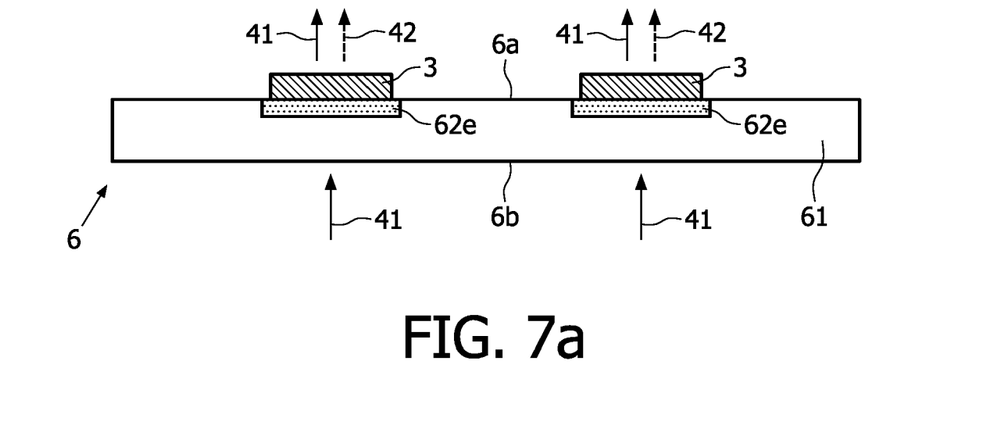
FIG. 7a: side view of another embodiment of the sample holder according to the present invention.
Figure 7B:
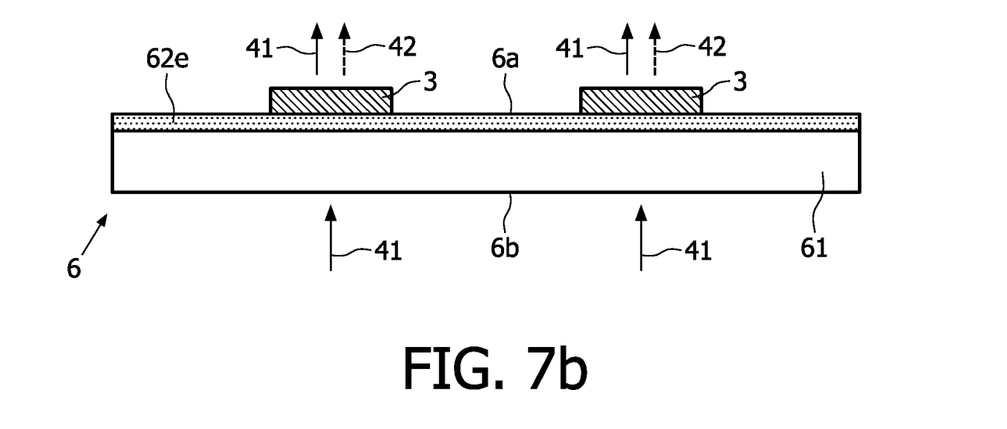
FIG. 7b: side view of another embodiment of the sample holder according to the present invention.
Figure 7C:
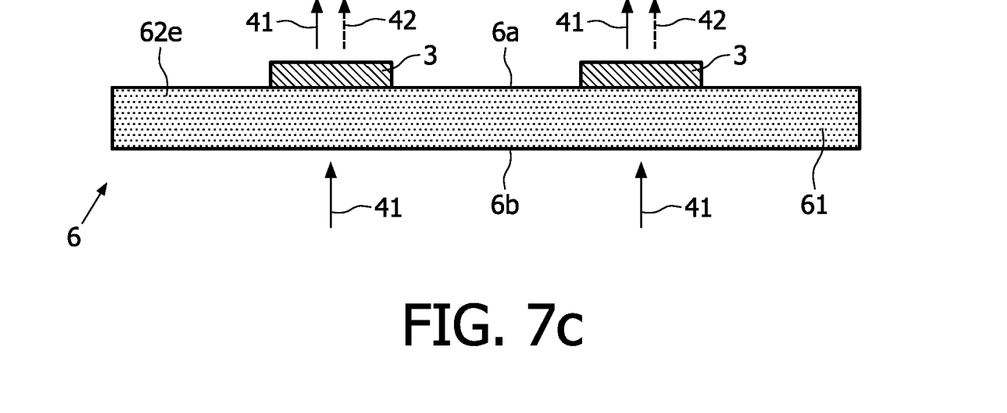
FIG. 7c: side view of another embodiment of the sample holder according to the present invention.

FIG. 7a-c show three other embodiments of the sample holder 6, where the prevention means 62e are arranged at least in the areas of the sample holder 6 covered with conversion elements 3. The prevention means 62e are non-transparent to at least secondary light 42, e.g. comprising a filter material absorbing secondary light 42 such as a phosphor of the general composition of

$(Lu_{1-x-y}Y_xGd_y)_{3-a-b}(Al_{1-m-n}Ga_mSc_n)_5O_{12}:Ce_aPr_b)$ with $0 \leq x \leq 1$, $0 \leq y \leq 0.5$, $0.001 \leq a \leq 0.02$, $0.001 \leq b \leq 0.005$, $0 \leq m \leq 0.5$, and $0 \leq n \leq 0.5$, and/or a phosphor of the composition of A) $(Ca_{1-x-y}Sr_x)S:Eu_y$ with $0 \leq x \leq 1$, $0.0003 \leq y \leq 0.01$;

B) $(Ba_{1-x-y}Sr_xCa_y)_{2-z}Si_{5-a}Al_aN_{8-a}O_a:Eu_z$ with $0 \leq x \leq 0.5$, $0 \leq y \leq 0.8$, $0.0025 \leq z \leq 0.05$, $0 \leq a \leq 1$; or C) $(Ca_{1-x-y}Sr_xMg_y)_{1-z}Si_{1-a}Al_{1+a}N_{3-a}O_a:Eu_z$ with $0 \leq x \leq 0.5$, $0 \leq y \leq 0.2$, $0.003 \leq z \leq 0.05$, $0 \leq a \leq 0.02$.

However, it is obvious that in such embodiments the prevention means 62e must be at least partly transparent to primary light 41 in order to achieve a down-conversion of primary light 41 by the conversion elements 3. In FIG. 7a, the prevention means 62e are essentially located only in areas covered with conversion elements 3. In FIG. 7b, the prevention means 62e are arranged as a continues layer at the surface 6a of he sample holder facing towards the conversion elements 3 conversion elements 3. In this embodiment, in addition to the areas as shown in FIG. 7a, also areas between the conversion elements comprise prevention means 62e. The thickness $D_P$ of the prevention means should be adapted according to the secondary light absorbing properties of the used material for the prevention means 62e. The transmission for secondary light of all prevention means 62a, 62b, 62c, 62d from one side to the other side of the prevention mean should be below 5%, preferably lesser than 1%, more preferred lesser than 0.1%. In FIG. 7c, the whole sample holder 6 is arranged as a prevention mean 62e. For example, the whole sample holder 6 may be made of material absorbing secondary light. Here the transmission criteria apply for the transmission of secondary light 42 from one conversion element 3 to a neighbored conversion element 3 via the sample holder 6.

Figure 8:
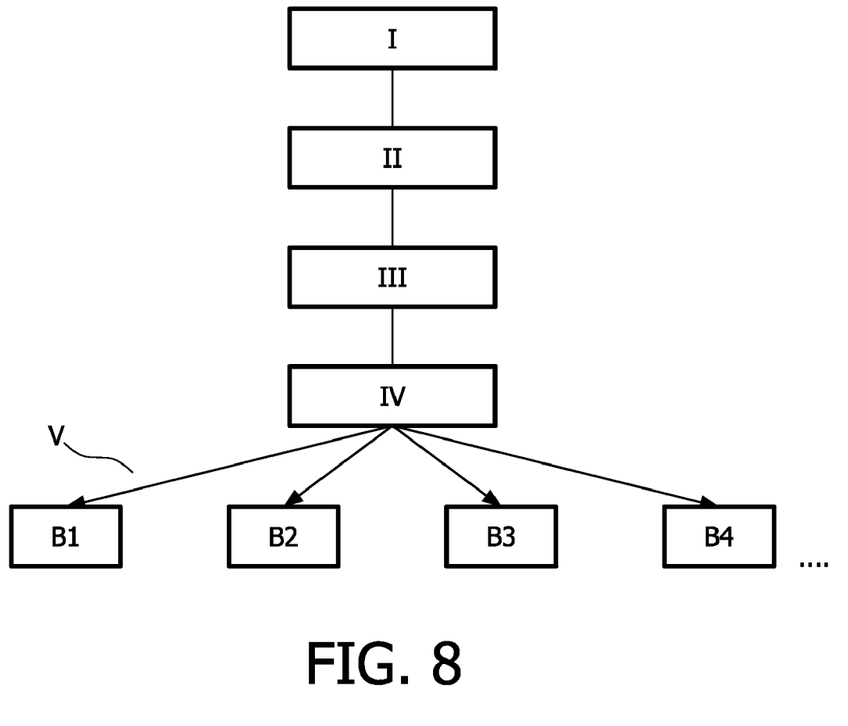
FIG. 8: schematic diagram of the method to determine the light conversion power.

In FIG. 8, the essential steps of the method to determine the conversion power of conversion elements 3 are schematically shown. Step I indicates the mounting of the multitude of conversion elements 3 on the sample holder 6. The mounting may be performed subsequently for each conversion elements or simultaneously with a suitable placing machine or as a sheet of non-separated conversion elements. However, before starting the measurements, the conversion elements 3 have to be separated from each other. During the mounting procedure the sample holder 6 may be already in the right position to start the measurements or has to be placed within the area of the light beam emitted by the light source 5 comprising primary light 41. Subsequently, in step II the sample holder 6 will be illuminated at least with primary light 41. If the light source 5 additionally emits wavelengths with the wavelength range of the secondary light, a filter has to be placed with the light beam emitted by the light source 5. In step III the intensities of primary and secondary light are determined. In step IV, the conversion power of each conversion element mounted 3 on the sample holder 6 is determined and assigned to the corresponding conversion element 3. For example, an identification number of an individual conversion element and the corresponding conversion power may be stored in a memory and/or transferred to a placement machine. In step V, the conversion elements are classified according to their determined conversion powers. The classification denotes the assignment of a classification number to each conversion element. The conversion elements are de-mounted from the sample holder and stored according to their conversion powers. For example in boxes, where all conversion elements are placed with a conversion power within a certain range. This procedure is also called binning, the certain conversion power range are so-called BIN-classes B1, B2, B3, B4 etc. Suitable handling machines/robots to mount, de-mount, move and/or store the individual conversion elements 3 according to their associated conversion powers are known by people skilled in the art.

In a preferred embodiment the measurements are performed simultaneously by a suitable detector elements as described earlier. In another embodiment, the mounting step comprises a first step mounting a sheet of non-separated conversion element onto the sample holder and a second step, where the individual conversion elements are separated from each other, e.g. by dicing. The dicing procedure is continued after separating the conversion elements 3 leading to grooves in the sample holder 6 beneath the conversion elements 3 serving as prevention means 62e.

Figure 9:
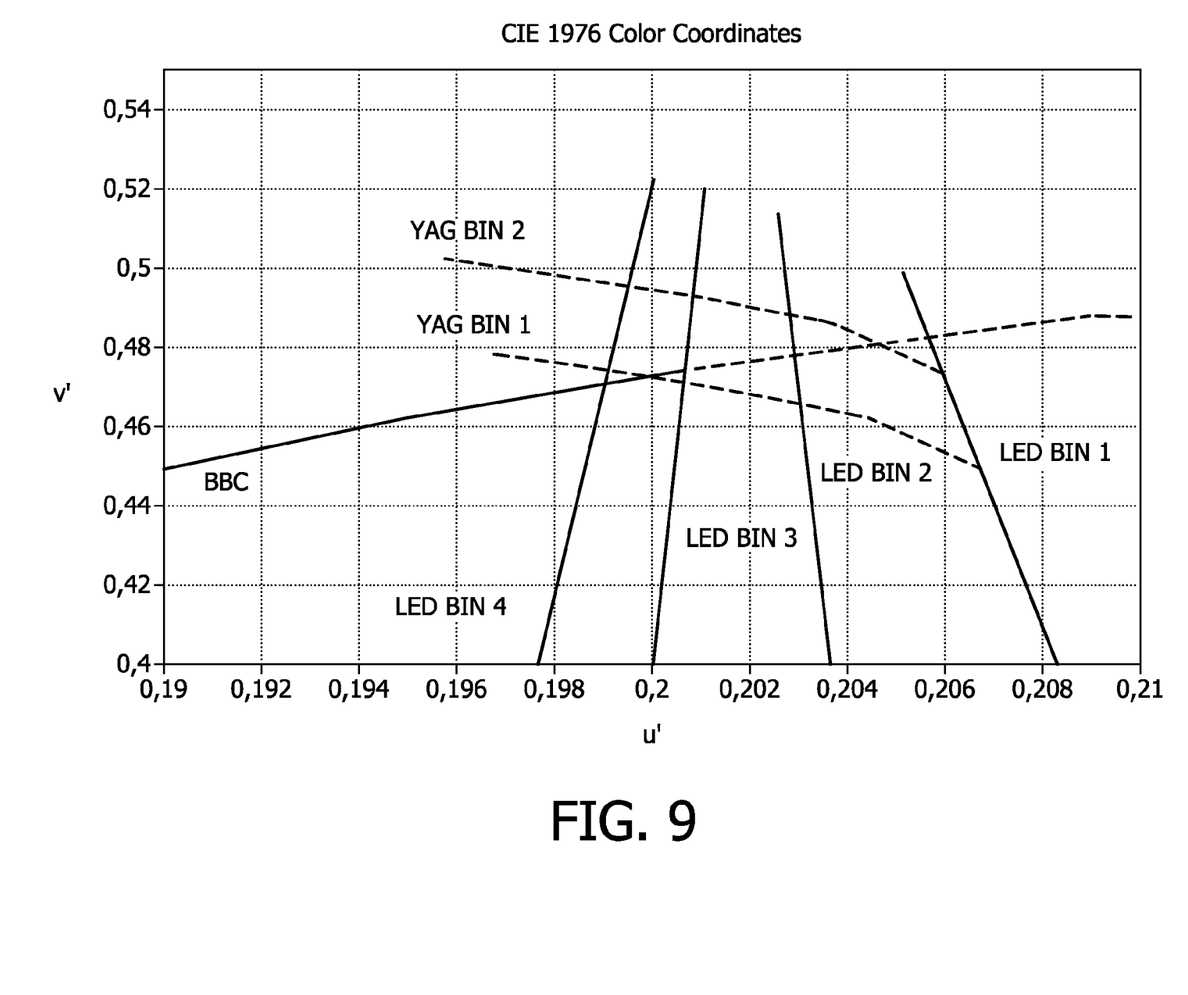
FIG. 9: color points as a function of peak wavelength of primary light and conversion power of conversion elements.

FIG. 9 schematically shows how conversion elements 3 can be assigned to LEDs 2 in order to emit light 4 of a certain color point after mounting both components together as pcLED. The conversion elements comprise phosphor materials, where the specific absorption coefficients vary with the excitation wavelength. However this variation is purely determined by the known and fixed phosphor—and host material of the conversion element. The solid lines indicated by LED BIN 1-4 are the color points given in u'v' coordinates of virtual pcLEDs with four different peak wavelengths of the primary LED light as a function of the conversion power of the corresponding conversion elements. Here, u'v' (CIE UCS 1976 color space) denote the well known parameters u'=f(x,y) and v'=f2(x,y) with x,y as the parameter of the CIE 1931 color space chromaticity diagram. The lower end point of the lines LED BIN 1-4 (outside the u'v' area in FIG. 9) corresponds to the color point of the primary light of the LEDs respectively of pcLEDs with conversion power equal to zero. The upper end point of the lines LED BIN 1-4 corresponds to the color point of the secondary light emitted by conversion material used for the conversion element (also outside the u'v' area in FIG. 9) or to a pcLED with full color conversion, where 100% of the primary light is down-converted to secondary light. The color points between the upper and lower end points are the color points of pcLEDs with increasing conversion power for conversion elements with the same conversion material. All 4 lines end up in the same point, if the same conversion material is used for the pcLEDs. The color point is a function of peak wavelength of the primary light, the conversion properties of the conversion material (absorption and emission spectrum) and the conversion power of the conversion elements. The conversion power of any conversion element additionally to the conversion material as such is determined by the concentration of the conversion material with the conversion element, the quantum efficiency, light transmission and light scattering properties of the conversion element. The latter parameters are hardly varying with the excitation wavelength, here represented by the peak wavelength of the primary light. From the determined conversion power at a certain excitation wavelength (e.g. a certain peak wavelength of the primary light), the conversion power for other peak wavelengths can be deduced as shown in FIG. 9. The dashed lines A and B in FIG. 9 are the color points (u'v') as a function of peak wavelength for a conversion element with a lower conversion power (A) and a higher conversion power (B). To calibrate the allocation procedure of LED and conversion elements, one has to determine one color point curve for one certain conversion power as a function the excitation wavelength (e.g. peak length of primary light), e.g. curve A. A calibration curve is required to include the additional but almost constant influence of pcLED packaging, e.g. the application of caps and other optical components mounted on top of the combination of LED and conversion element, which is a negligible source of color point variations during mass production. Corresponding curves for conversion elements with other conversion powers will result in curves parallel the calibration curve A. Therefore, it is only required to know the accurate conversion power at one primary wavelength to deduce the resulting color point after combination with an LED of any other peak wavelength of the primary light. However, this is only valid in case of exciting the same electronic transitions in the conversion material. The black body curve in FIG. 9 is denoted by BBC.

Figure 10:
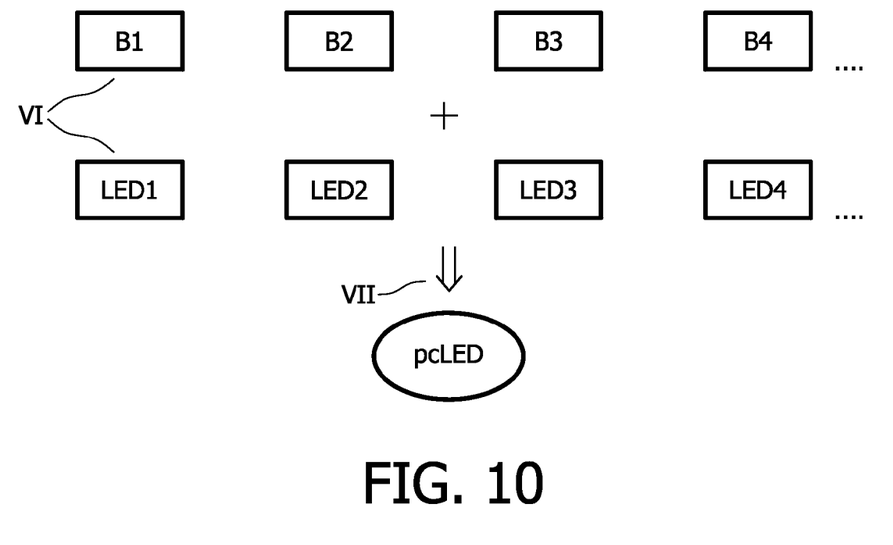
FIG. 10: schematic diagram of the method for producing a multitude of pcLEDs according to the present invention.

FIG. 10 schematically describes the method to allocate conversion elements with a certain conversion power to LED with a certain peak wavelength in order to obtain a pcLED with the desired color point. Applying this method results in a mass production of pcLEDs with marginal color point variations between different pcLEDs within this production batch. The conversion powers of conversion elements are measured with the device according to our invention are classified in so-called BIN-classes B1, B2, B3, B4 etc. Also the LEDs are classified for example according to their peak wavelength of the primary light in so-called BIN-classes LED1, LED2, LED3, LED4 etc. Alternatively to the peak wavelength the LED classification may be done according to other parameters characterizing the spectrum of the primary light, e.g. to their emission band position.

As an example, the combination of binned "blue" LEDs and binned "yellow" polycrystalline ceramics conversion elements (YAG:Ce with 0.4 wt % Ce, density of 99% of the theoretical solid state body density, thickness of 120 µm in light emission direction) resulted in white pcLEDs with target color point and an overall spread of $\Delta u'v'<0.01$.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

The invention claimed is:

1. Device for determining the light conversion power of a multitude of conversion elements for phosphor converted LEDs, the device comprising:
    a sample holder,
    a light source for illuminating the sample holder with a primary light, the sample holder being at least locally transparent for the primary light and configured for mounting the multitude of conversion elements, the conversion elements being configured to at least partially convert the primary light into a secondary light with a wavelength longer than the primary light, the sample holder further comprising a prevention means for preventing a light guiding of the secondary light from one mounted conversion element through the sample holder to another mounted conversion element,
    a detector element for measuring the intensities of the primary light transmitted through the conversion elements and of the secondary light created within the conversion element for each conversion element separately, the detector element comprising at least a first filter transparent either for primary light or for secondary light; and
    a calculation means for calculating the conversion power from the ratio between the intensities of the primary and secondary light measured by the detector element.

2. Device according to claim 1, further comprising a diffuser plate arranged between the sample holder and the light source to facilitate illuminating the sample holder with diffuse primary light.

3. Device according to claim 2 wherein the diffuser plate comprises a material, which absorbs secondary light.

4. Device according to claim 1, wherein the detector element comprises a CCD camera with a sufficient lateral resolution to determine the intensities of primary and/or secondary light for each conversion element simultaneously.

5. Device according to claim 1, wherein the prevention means comprises at least one or more elements of the group of material absorbing at least the secondary light, a reflective material or a light scattering material with suitable scattering properties at least for secondary light.

6. Device according to claim 1, wherein the prevention means are grooves defined within the sample holder.

7. Device according to claim 1 wherein the prevention means is a filter not transparent to secondary light.

8. Device according to claim 7, wherein the prevention means extends over the entire sample holder.

9. Method for determining the light conversion power of conversion elements with a device comprising a light source, a sample holder and a detector element according to claim 1 the method comprising the steps of:
    mounting the multitude of conversion elements on the sample holder,
    illuminating the sample holder with mounted of conversion elements,
    measuring the intensities of the primary light transmitted through each of the conversion elements and the secondary light emitted from each of the conversion elements,
    determining the conversion power of each conversion element resulting from the ratio between the measured intensities of primary and secondary light of each conversion element, and
    classifying the conversion elements according to their conversion power.

10. Method according to claim 9, wherein the intensities of the primary and the secondary light of each conversion element are measured simultaneously.

11. Method according to claim 9, wherein the step of mounting of the multitude of conversion elements further comprises the steps of:
    mounting of a sheet of conversion elements on the sample holder, and
    separating the conversion elements and preparing grooves within the sample holder by dicing.

12. Method for producing a multitude of pcLEDs with essentially the same color point, the method comprising the steps of:
    classifying LEDs according to the peak wavelengths of their primary light,
    allocating the LEDs with conversion elements with a conversion power suitable to obtain a certain color point determined by applying a device for determining the light conversion power of a multitude of conversion elements for phosphor converted LEDs comprising a light source, a sample holder, a detector element, and a calculation means, wherein the applying step comprises:
    mounting the multitude of conversion elements on the sample holder,
    illuminating the sample holder with mounted of conversion elements,
    measuring the intensities of the primary light transmitted through each of the conversion elements and the secondary light emitted from each of the conversion elements,
    determining the conversion power of each conversion element based at least in part on the ratio between the measured intensities of primary and secondary light of each conversion element,
    classifying the conversion elements according to their conversion power, and
    mounting together the allocated conversion elements and LEDs in order to obtain a multitude of pcLEDs with essentially the same color point.

* * * * *